United States Patent [19]
Haas et al.

[11] Patent Number: 6,074,414
[45] Date of Patent: Jun. 13, 2000

[54] SYSTEM FOR PROVIDING THERMAL APPLICATION TO EXTERNAL BODY AREAS OF A PATIENT

[75] Inventors: Michael Haas, Covington; Richard Bailey, Mandeville, both of La.; Lee Barberito, Corpus Christi, Tex.; Jerome F. Krentel; Michael Haas, II, both of Covington, La.

[73] Assignee: Limex Bio-Tech L.C., Louington, La.

[21] Appl. No.: 09/130,007

[22] Filed: Aug. 6, 1998

[51] Int. Cl.⁷ ....................................................... A61F 7/00
[52] U.S. Cl. .......................... 607/108; 607/111; 607/112; 607/114
[58] Field of Search ............................. 607/96, 108–112, 607/114, 104

[56] References Cited

U.S. PATENT DOCUMENTS

| | | |
|---|---|---|
| 3,871,117 | 3/1975 | Richmond et al. . |
| 4,005,531 | 2/1977 | Weintraub et al. . |
| 4,432,363 | 2/1984 | Kakegawa . |
| 4,937,435 | 6/1990 | Goss et al. . |
| 4,987,896 | 1/1991 | Nakamatsu . |
| 5,097,828 | 3/1992 | Deutsch . |
| 5,190,539 | 3/1993 | Flecher et al. . |
| 5,269,369 | 12/1993 | Faghri ...................................... 607/104 |
| 5,591,162 | 1/1997 | Fletcher et al. . |
| 5,653,741 | 8/1997 | Grant . |
| 5,725,049 | 3/1998 | Swanson et al. ................... 165/104.26 |

OTHER PUBLICATIONS

Brown Medical Industries Heel Huggers solication; Brown Medical Industries Homepage; on the Internet Sep. 23, 1996.

Orthomerica Products, Inc. solicitation for Plantar Fasciitis Night Splints; on the Internet Sep. 24, 1996.

Mitchel, Idol R et al; Deep Fascia of the Foot; Jrnl Am Podiatric Medical Assoc, vol. 81, No. 7, pp. 373–378.

Daly, Peter J. et al; Plantar Fasciotomy for Intractable Plantar Fasciitis. .; Foot and Ankle, vol. 13, No. 4 May '92 pp. 188–195.

Schepsis et al; Plantar Fasciitis—Etiology, Treatment, Surgical Results, and Review. .; Clinical Orthopaedics and Related Research; No. 266, May, 1991, pp. 185–196.

Warren, Barbara L.; Plantar Faciitis in Runners. .; Sports Medicine Oct. 5, 1990; pp. 338–345.

Gill, Lowell H.; Plantar Faciitis: Diagnosis and Conservative Management; Jrnl Am Acd Orthopaedic Surgeons;V5 N2 Mar. 1997 pp. 109–117.

Hough, David; Ice is Important for Curing Injuries; Mississippi State University homepage www.educ.msu.edu; Spotlight, Fall, 1994.

*Primary Examiner*—Linda C. M. Dvorak
*Assistant Examiner*—Roy Gibson
*Attorney, Agent, or Firm*—Joseph T. Regards, Ltd.

[57] ABSTRACT

A thermal applicator for medical use which is worn upon or applied directly to the body of a patient to modify its temperature for therapeutic treatment. The preferred embodiment of the present invention contemplates the utilization of a heat pipe having first and second ends and a length, the first and second ends communicating with first and second thermally conductive plates, respectively, the first thermally conductive plate configured to communicate with an exterior portion of the body of the patient and to provide localized thermal treatment, the second thermally conductive plate placed at an area removed from the area to be treated, and configured to accept, for example, an ice pack (or other thermal material or apparatus) to affect a change in the temperature of the second thermally conductive plate, cooling the second end of the heat pipe and allowing the heat pipe to cool the first thermally conductive plate, thereby providing localized cooling of the area to which it is applied. An alternative embodiment of the invention contemplates a heat source in lieu of the ice pack, wherein the second thermally conductive plate would function as an evaporator, thereby providing a reverse cycle in the heat pipe, for heating the area to be treated via the first thermally conductive plate. The present invention may be utilized for localized thermal application on various parts of the body, and several examples are illustrated, including an exemplary system to treat plantar fasciitis.

30 Claims, 8 Drawing Sheets

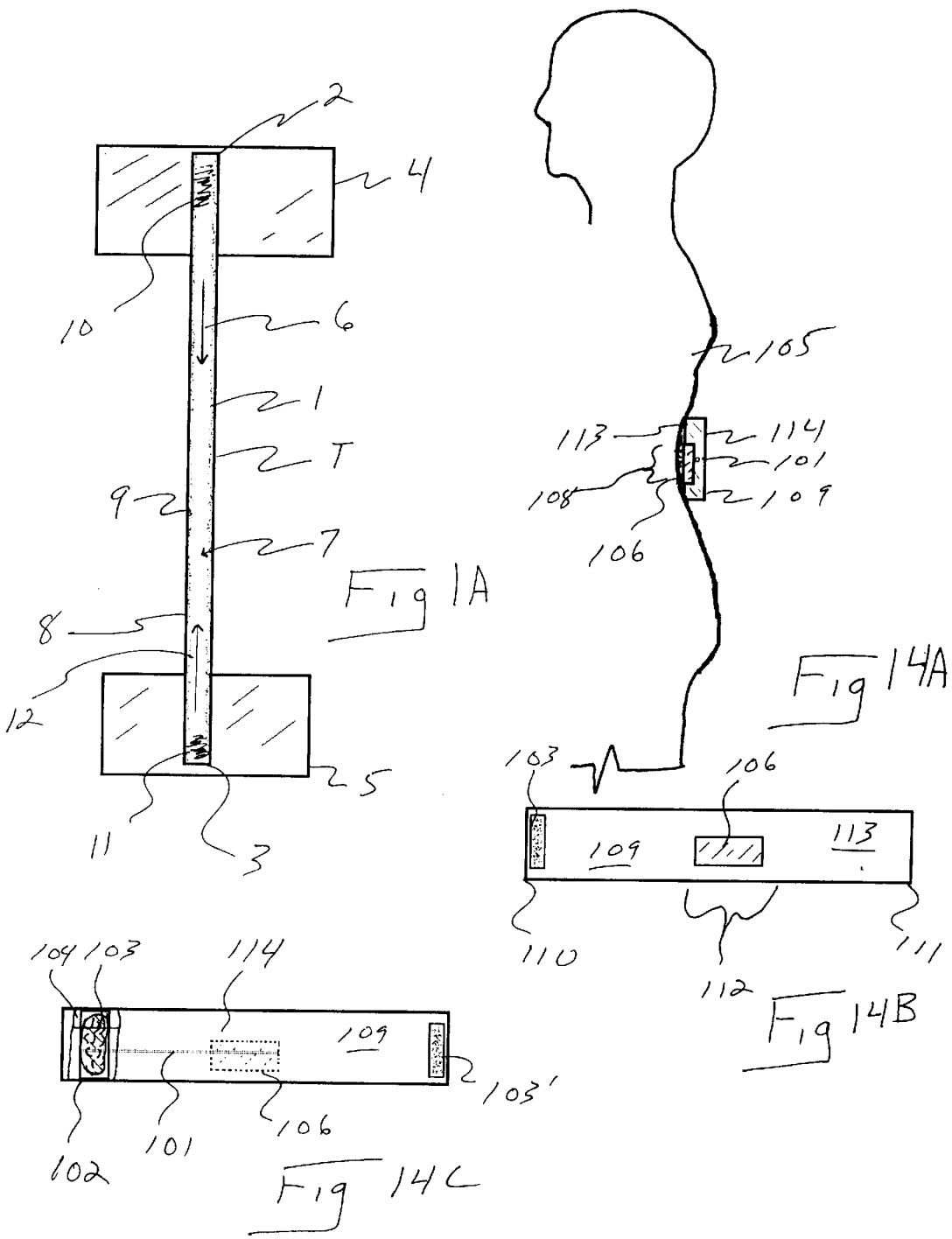

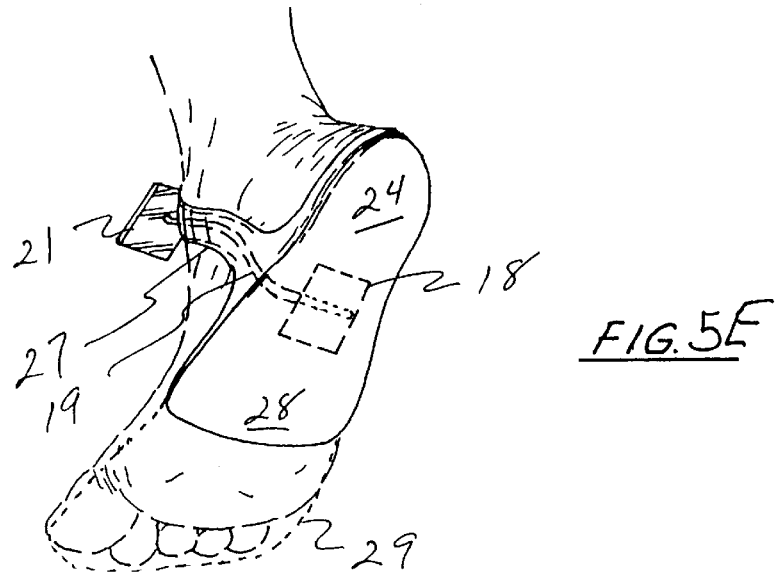
FIG. 5E
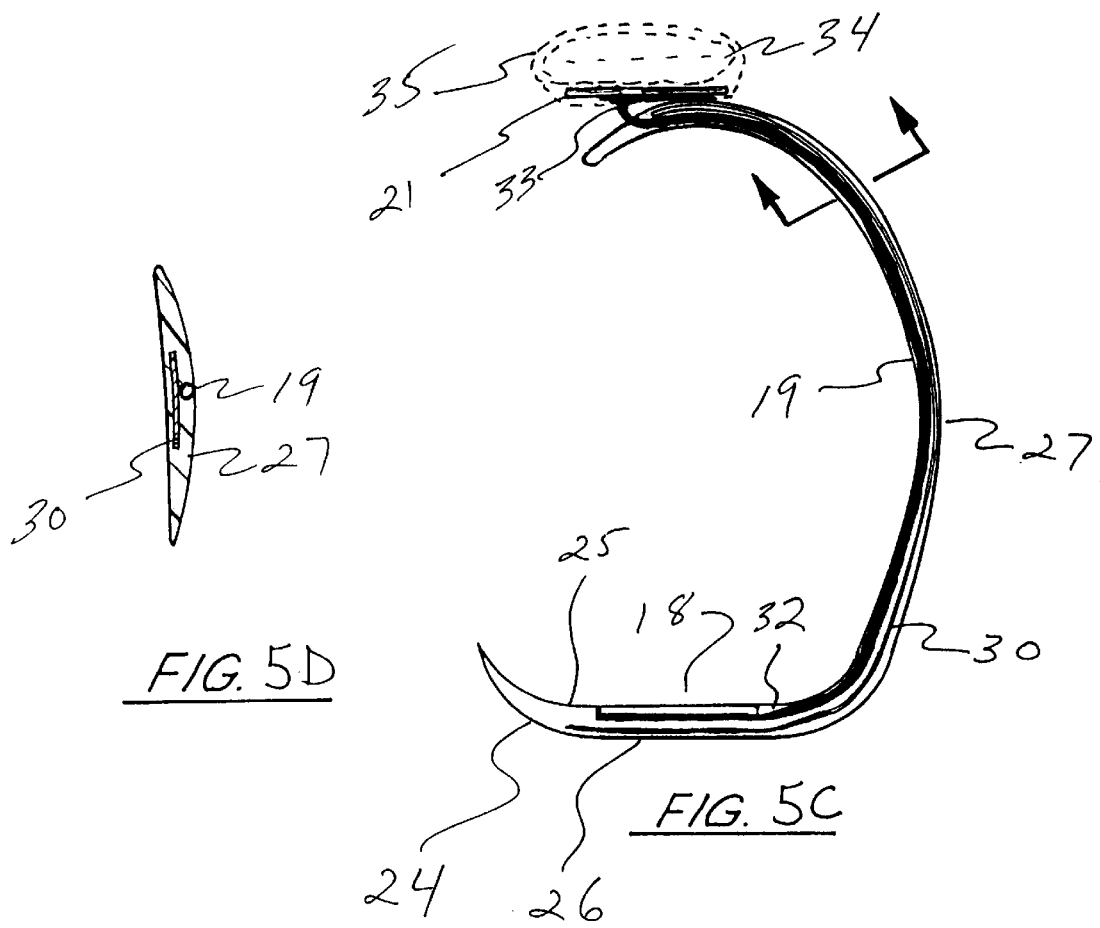
FIG. 5D
FIG. 5C

SYSTEM FOR PROVIDING THERMAL APPLICATION TO EXTERNAL BODY AREAS OF A PATIENT

TECHNICAL FIELD OF THE INVENTION

The present invention relates to thermal applicators for medical use, and in particular to apparatus and systems worn upon or applied directly to the body of a patient to modify its temperature for therapeutic treatment.

The preferred embodiment of the present invention contemplates the utilization of a heat pipe having first and second ends and a length, the first and second ends communicating with first and second thermally conductive plates, respectively, the first thermally conductive plate configured to communicate with an exterior portion of the body of the patient and to function, in the preferred embodiment, as an evaporator plate for heat exchange, to provide localized thermal treatment, the second thermally conductive plate placed at an area removed from the area to be treated, and configured to accept, for example, an ice pack (or other thermal material or apparatus) to affect a change in the temperature of the second thermally conductive plate, in the exemplary case causing it to function as a condenser, cooling the second end of the heat pipe and allowing the heat pipe to cool the first thermally conductive plate, thereby providing localized cooling of the area to which it is applied.

An alternative embodiment of the invention contemplates a heat source in lieu of the ice pack, wherein the second thermally conductive plate would function as an evaporator, thereby providing a reverse cycle in the heat pipe, for heating the area to be treated via the first thermally conductive plate.

The present invention may be utilized for localized thermal application on various parts of the body, and several examples are illustrated, including an exemplary system to treat plantar fasciitis which allows the patient full mobility and comfort during treatment, at a level of performance unknown in the prior art.

BACKGROUND OF THE INVENTION

The technique of thermal application to external body parts for medical treatment is ancient, with literally thousands of patents and publications teaching the application of heat or cold to localized areas of the body utilizing heating pads, ice packs, or other materials or devices.

Examples of patents that may be of at least some cursory relevance to the present invention include:

| Patent Number | Inventor | Date of Issue |
| --- | --- | --- |
| 5653741 | Grant | 08/05/1997 |
| 5591162 | Fletcher | 01/07/1997 |
| 5431622 | Pyrozyk et al | 07/11/1995 |
| 5331688 | Kiyohara | 07/26/1994 |
| 5190539 | Fletcher | 03/02/1993 |
| 5097828 | Deutsch | 03/24/1992 |
| 4937435 | Goss et al | 06/26/1990 |
| 4860748 | Chiurco | 08/29/1989 |
| 4614191 | Perler | 09/30/1986 |
| 4432363 | Kakegawa | 02/21/1984 |
| 4005531 | Weintraub | 02/01/1977 |
| 3871117 | Richmond et al | 03/18/1975 |

Plantar Fasciitis is a common condition in humans caused by an inflammation of the arch muscle or large ligament beneath the foot. Common treatment methods include surgery, shoe orthotics, as well as the application of heat or cold packs thereto. However, the utilization of conventional ice packs or other devices for providing localized thermal application require the user to remain relatively stationary, and are thereby inconvenient and troublesome to use.

There has been some development of gel insoles which might be cooled and placed into the shoe of the user, but such is not contemplated in the present therapy, and would not work satisfactorily, as the insole would generally equalize to the temperature inside the shoe in a short time. See, for example, U.S. Pat. No. 3,871,117, or, for heating, U.S. Pat. No. 5,331,688 for an insole foot warmer. U.S. Pat. No. 4,005,531 teaches a shoe having a sole adapted to receive a "cool container" of ice or the like.

However, the prior art is not believed to teach a system which provides a portable thermal effect to the area to be treated, which allows the user to remain mobile and comfortable, while providing a relatively consistent, regulated temperature application.

Heat pipes are believed to have been developed in conjunction with the U.S. Space Program, and contemplate a relatively simple and efficient, yet high tech approach at providing thermal transfer from one location to another. Now commonly utilized in the computer industry to transfer heat away from a computer chip in an isolated location, for example, in a laptop computer, to a heat sink, heat pipes heave not been found to be utilized extensively in other fields, including medicine.

Such use in medicine appears to have been limited to cryogenic probes and the like, for localized hypothermic (or in come cases hyperthermic) therapies within the body, such as U.S. Pat. No. 5,591,162 for treatment of cancer tumors, nerve injuries, etc. Also see U.S. Pat. No. 4,432,363 (heat pipe used to transmit energy to recharge a pacemaker battery), and U.S. Pat. No. 5190539 (heat pipe catheter).

In addition to ice packs and heating pads, the prior art contemplates other, more sophisticated thermal devices, such as, for example, Peltier effect solid state heating or cooling systems which generally include a heat sink placed in communication with the body. In addition, there has been taught "soft" Pelteir effect pads, some contemplating metal fabric or mesh U.S. Pat. Nos. 4,937,435, 5,653,741 and 5,097,828, as opposed to solid metal sinks.

However, none of the prior art devices taught, contemplated, or suggested the system of the present invention, which allows localized thermal application to various parts of the body, without reducing mobility or use of that body part.

GENERAL SUMMARY DISCUSSION OF THE INVENTION

Unlike the prior art, the present invention provides a thermal applicator worn upon or applied directly to the body which is more effective and easier to utilize, allowing the patient full mobility and comfort.

A treatment which is particularly suited for the present invention is that for a condition known as plantar fasciitis, a condition where the ligaments and tendons in the foot are inflamed and swollen, causing significant pain. Conventional treatments include surgery and medication, the best non-invasive therapy including the application of a cold surface to the bottom of the foot, and cooling same to a temperature of 60–65 degrees Fahrenheit for a period of time.

The problem with conventional methods of cooling, including ice packs and Peltier effect devices, is that they are cumbersome and require the patient to rest in a stationary position while applying the cold. There are gel and other composition insoles which may be cooled then placed in a shoe and worn, such as the HEEL HUGGER by Brown Medical Industries, but these devices are believed to be of only limited use, as the coolant quickly is brought up to skin temperature, or the coolant supply is so bulky as to prevent use of the foot.

The preferred embodiment of the present invention contemplates the utilization of a heat pipe having first and second ends and a length, the first and second ends communicating with first and second thermally conductive plates, respectively, the first thermally conductive plate configured to communicate with an exterior portion of the body of the patient and to function, in the preferred embodiment, as an evaporator plate for heat exchange, to provide localized thermal treatment, the second thermally conductive plate placed at an area removed from the area to be treated, and configured to accept, for example, an ice pack (or other thermal material or apparatus) to affect a change in the temperature of the second thermally conductive plate, in the exemplary case causing it to function as a condenser, cooling the second end of the heat pipe and allowing the heat pipe to cool the first thermally conductive plate, thereby providing localized cooling of the area to which it is applied.

The heat pipe is a passively controlled, gas loaded heat transfer device which has a longitudinal conduit formed therein charged with a working refrigerant such as water under a partial vacuum, or ammonia, methanol, nitrogen, or the like. One end forms the evaporator, and the other end forms the condenser, although one end may be utilized for the other; that is, there is no fixed evaporator or condenser end. The heat pipe works on a two phase cycle, that is, the working fluid evaporates at the heat source, cooling same, and condenses at the cooling source. The heat pipes currently utilized are formed of a copper pipe having about a 4 mm (3/16 inch) diameter and a length of up to about ten inches, and were supplied by THERMACORE. The copper allows for some bending of the heat pipe for configuring the unit to the appropriate application, although the heat pipe is not actively flexible per se, although it is believed that an actively flexible unit will be available in the future, and would be quite useful in the present invention.

The present device can be configured to fit a variety of parts of the body, including application to the foot in a variety of locations in a manner to allow the continued wearing and use of footwear during treatment, including application to the base of the foot, arch, heel, between the arch and heel, along the Achilles tendon, top of the foot, and elsewhere.

For use in treating plantar fasciitis, the first thermally conductive plate is placed generally between the heel and arch of the foot, and the heat pipe is run about the foot such that the second thermally conductive plate rests above the top of the foot. The heat pipe may be manipulated to allow the user to wear a shoe with this device, and the first thermally conductive plate may be built-into the top of an insole such that it is applied to the correct portion of the sole of the foot. Further, ready-made shoes or sandals, having the present device built into the shoe design, may be provided, such that the second thermally conductive plate is located away from the inner shoe area, so that ice or other refrigerant means may be provided thereon, and may be insulated thereabout to provide maximum thermal transfer.

The present design has been found to provide about 20–30 minutes of cooling of the subject foot with only a 1.5 ounce bag of ice affixed to the second thermal plate and enveloped by neoprene foam, which acted as a fastener and insulator. The embodiment provided constant thermal cooling of about 65 degrees, plus or minus 5 degrees Fahrenheit. The ice bag and outer, second thermal plate provided nominal hindrance to movement, while the heat pipe provided enhanced, regulated thermal transfer over a relatively extended period of time, whereas a conventional one ounce bag of ice directly applied to the skin would have cooled the skin to a much cooler temperature, which is undesirable, and would have melted in only a few minutes.

An alternative embodiment of the invention contemplates a Peltier effect device in lieu of an ice pack. Another embodiment contemplates a hear source in lieu of the ice pack, wherein the second thermally conductive plate would function as an evaporator, thereby providing a reverse cycle in the heat pipe, for heating the area to be treated via the first thermally conductive plate.

The present invention may be utilized for localized thermal application on various parts of the body, and built into splints, casts, belts, straps, and garments, shoes, etc., and the first thermal conductive plate may comprise a "soft", anatomically conforming, thermally conductive material, such as thermal putty, metal mesh (such as copper wire braid), etc.

It is therefore an object of the present invention to provide a system for localized thermal treatment of a patient which is effective, comfortable, and mobile.

It is another object of the present invention to provide a thermal treatment device which is easy and safe to use, and efficient in operation, providing regulated thermal transfer.

It is still another object to provide a method of treating plantar fasciitis utilizing a device which may be worn in conjunction with footwear by a patient, allowing full mobility, yet providing thermal treatment for an adequate period of time with no replenishing of the thermal source.

It is another object of the present invention to provide a thermal device which may be utilized with a variety of devices worn by a patient, including shoes, belts, garments, splints, bandages, and casts.

Lastly, it is an object of the present invention to provide a method of cooling a localized, exterior part of a patients body, wherein the thermal source is removed from the application area, and there is provided therebetween a heat pipe for providing temperature regulation and transmission.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1A illustrates the basic components of the present invention, including the heat pipe and evaporator and condenser plates.

FIG. 5 illustrates a side view of the invention of FIG. 1, the device integrated into an insole, which insole further extends about the heat pipe, which rises above the foot to allow the wearing of footwear.

FIG. 5C is a partially cross-sectional view of the invention of FIG. 5A, illustrating the placement of the heat pipe and evaporator plate vis-a-vis the insole.

FIG. 5D is a lateral, cross sectional view of the invention of FIG. 5C.

FIG. 5E is a bottom view of the invention of FIG. 5A, illustrating a food insole in phantom.

FIG. 14A illustrates a cross sectional view of the back belt embodiment of the present invention, illustrating the belt having the evaporator plate in contact with the a patient's lower back area, and the heat pipe situated thereupon.

FIG. 14B illustrates a view of the inside of the belt of FIG. 14A, illustrating the evaporator plate location on the belt.

FIG. 14C illustrates a view of the outside of the belt of FIG. 14A, illustrating an exemplary location of the condenser plate, and illustrating the heat pipe and evaporator plate in phantom.

DETAILED DISCUSSION OF THE INVENTION

Figure 3:
FIG. 3 illustrates an opposing side view of the invention of FIG. 2.
Figure 2:
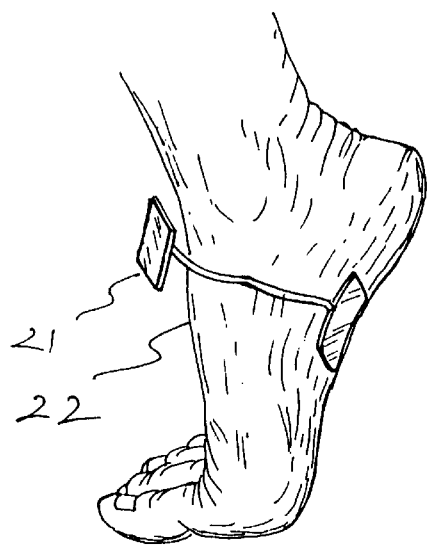
FIG. 2 illustrates a side view of the invention of FIG. 1.
Figure 4:
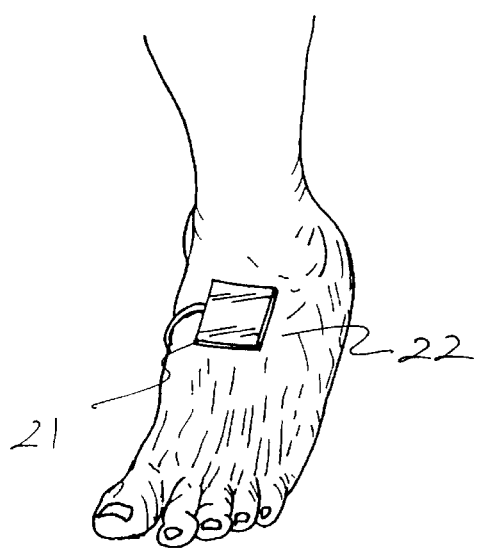
FIG. 4 illustrates a frontal view of the invention of FIG. 1.
Figure 1:
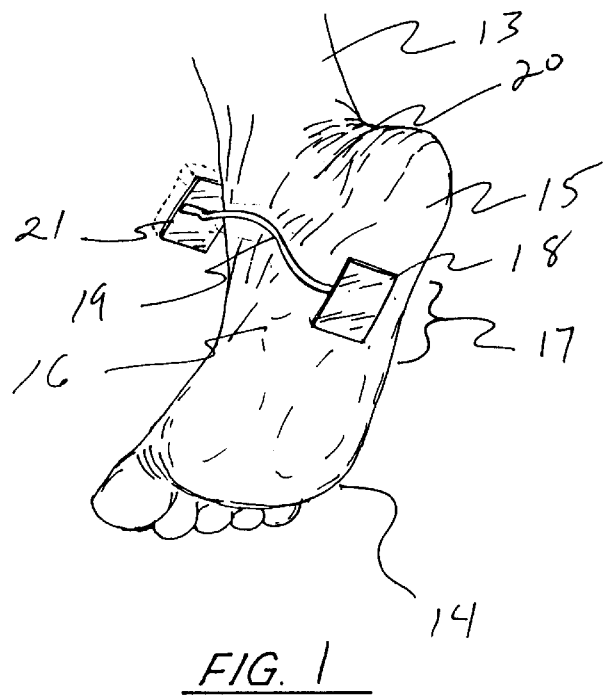
FIG. 1 illustrates an exemplary embodiment of the invention configured to treat plantar fasciitis, showing the heat pipe having first and second ends communicating with evaporator and condenser plates, respectively, the evaporator plate communicating with the sole of the foot, the condenser plate located in a position removed from the foot to allow for the wearing of footwear.

Referring to FIG. 1A, the thermal device T of the present invention comprises a heat pipe 1 having a conduit 7 formed therethrough having inner walls 8, the heat pipe further having first 2 and second 3 closed ends. The first 2 and second 3 ends have situated thereupon first and second plates which, in the present example, form an evaporator plate 4 and a condenser plate 5, respectively, of thermally conductive material. It is preferred that the heat pipe run the lengths of the evaporator and condenser plates, if possible, to maximize heat transfer from the plates to the heat pipe, for the highest efficiency transfer.

As earlier indicated, the heat pipe currently utilized is an off-the-shelf product commonly available and marketed under the trade name THERMACORE, and comprises a capillary or wicking material coating the inner walls 8 of conduit 7, the heat pipe further containing in conduit 7 an appropriate working refrigerant which would evaporate and condense at the working temperatures of the evaporator plate and condenser plate, respectively, such as, for example, water under a partial vacuum, ammonia, methanol, although there are other refrigerants which may be utilized.

In use, a heat source, such as a patient's skin, is placed in the vicinity of the evaporator plate, causing same to heat, which in turn evaporates the refrigerant 10 at the evaporator plate, causing the gaseous refrigerant 6 to migrate away from the evaporator plate 4, where, upon reaching the condenser plate 5, which has situated in its vicinity a source of cold such as, for example, an ice pack, the gaseous refrigerant condenses to a liquid due to the decreased temperature. The liquid refrigerant is then carried away by the capillary action of the wicking or capillary material 9 coating the inner walls 8 of the conduit 7, carrying the liquid refrigerant back to the evaporator plate 4, where it is again evaporated. Each evaporation cycle utilizes heat, thereby cooling the evaporator plate.

While the present example, illustrates a cycle generated by heat from a patients skin and condensed by ice, it is noted that the same device may be utilized in a heating capacity, wherein the condenser plate is placed upon the patient's skin, and the evaporator plate is situated adjacent to a source of heat greater than the patient's skin. A refrigerant would be chosen which has an evaporation point commensurate with the temperature at the evaporator plate, which would be higher than the patients skin, and the refrigerant would have to have a condensation point commensurate with the temperature of the condenser plate. It is further noted that the evaporator and condenser plates are referred to in these terms by way of illustration, as either end (and either plate) can function as the evaporator or condenser plate, with the appropriate application of heat at one end, and cooling at the other.

Continuing with FIGS. 1–4, an exemplary application of the present invention relates to the treatment of plantar fasciitis which would allow the patient to remain mobile. As shown, the device is situated at the foot 14 of the patient 13 such that the evaporator plate 18 placed in communication with the skin of the patient in an area 17 generally between the heel 15 and arch 16 of the bottom of the foot, and the heat pipe 19 is conformed to run along the inner side 20 of the foot such that the evaporator plate 21 is situated generally above the top 22 of the foot. Although the evaporator plate may be placed in other areas, the present configuration appears to work best with the relatively rigid heat pipes currently available. When more flexible heat pipes come available, placement of the condenser plate may be more diverse.

Figure 5A:
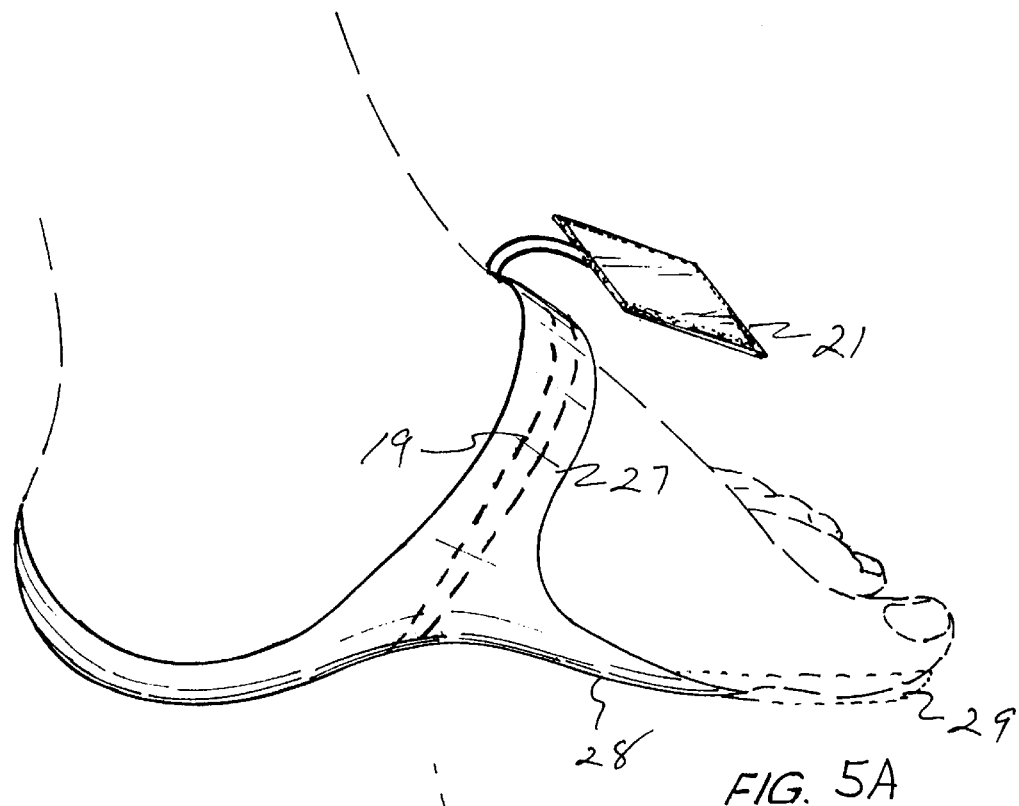
FIG. 5A illustrates a side view of the invention of FIG. 5, illustrating in phantom the image of a foot.

Beginning with FIGS. 5C and 5E, and referring to FIGS. 5A–5E, the present device is ideally supported and contained within an insole 24 assembly, which is configured to fit within footwear and support the foot, the insole having upper 25 and lower 26 sides, the upper side configured to engage the bottom of the foot, the lower side configured to engage the bottom of an item of footwear, or a sole. The insole may be formed of neoprene foam, or other commonly utilized material, and may include arch support or other features, and may be a partial 28 or full 29 size to engage the foot.

As shown, the insole 24 has integrated into the upper side 25 the evaporator plate 18, positioned to engage the foot between the heel and arch, as earlier discussed, for the treatment of plantar fasciitis, although it may be placed elsewhere to treat other conditions. Emanating from the side of the insole, and configured to run comfortably along the inside of the foot is vertical support 27, configured to envelope the heat pipe 19 (having first 32 and second 33 ends) running from the evaporator plate 18 to the condenser plate 21, which is configured to be situated above or along the top of the foot.

Further illustrated is a vertical support member 30 comprising, for example, an elongated, molded plastic piece running from the shank of the insole, along the vertical support, to support same and prevent undue bending of the heat pipe. The heat pipe and vertical support member are enveloped by the insole and vertical support, and the vertical support member may be fabricated of, for example, neoprene foam or the like to provide a soft, comfortable contact with the patient, or ideally another non-thermally conductive material, and to insulate the heat pipe, as illustrated in FIG. 5D.

Figure 5B:
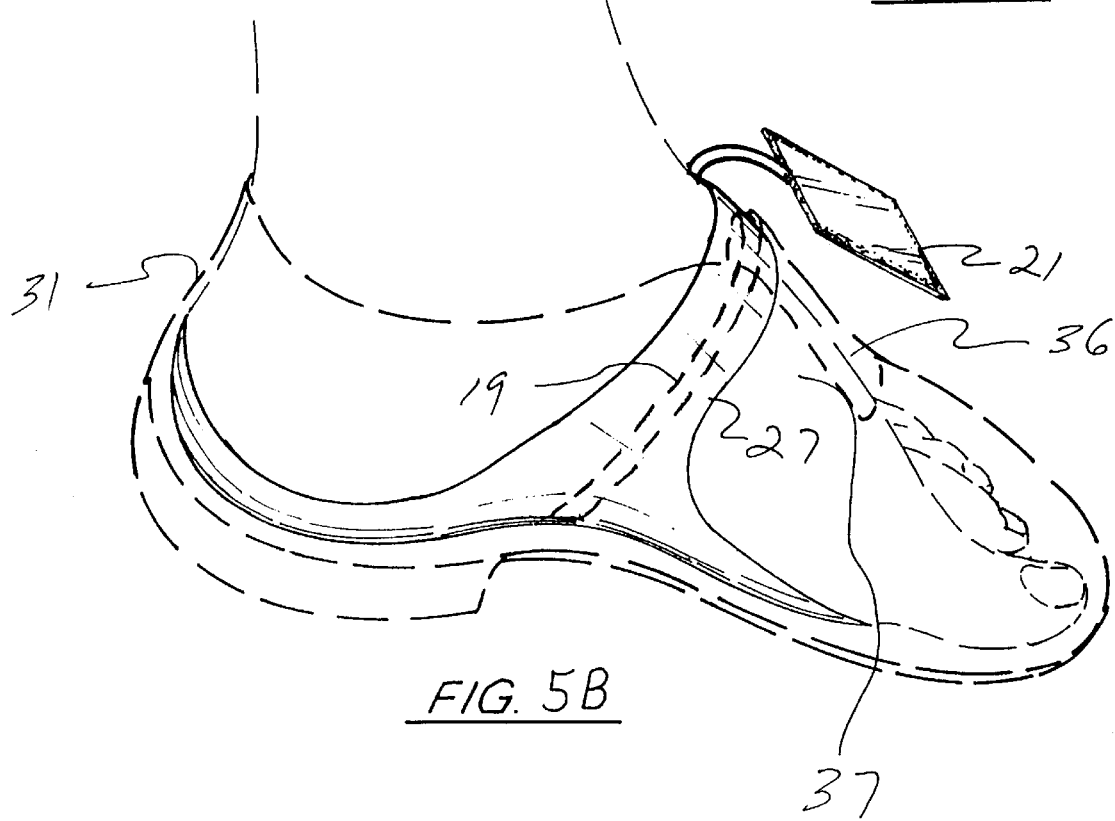
FIG. 5B illustrates in phantom an exemplary item of footwear worn in conjunction with the device of FIG. 5A.

In use, the insole 24 is configured to fit within an item of footwear, such that only the condenser plate emanates from between the tongue 36 and the tab 37 of a typical shoe (FIG. 5B). The patient would merely place the shoe upon the foot to be treated, and place a small bag of ice 34 or other coolant (which could comprise a material or device, for example, a Peltier device P as shown in phantom in FIG. 1) upon the condenser plate 21 (continuing with FIG. 5D), and retain the ice or coolant via sleeve or pouch 35, which may comprise, for example, insulating neoprene. With long clothing, a casual observer would likely not even notice the device in use.

Upon activation by placement of the coolant upon the condenser, the evaporator plate would almost immediately begin to cool down, in the present working embodiment, to around sixty to sixty-five degrees F, the ideal temperature for cold therapy in this situation. A typical treatment would entail about 20–30 minutes of consistent temperature exposure, which has been achieved in the present device with about a 1.5 ounce ice pack.

While the present embodiment shown illustrates an insole and shoe separately, it is averred that the device can be made part of an article of footwear, including, for example, a sandal, wherein the evaporator is built into the insole, and the heat pipe runs along the upper, supported structure, with the condenser plate situated on the exterior of the shoe, and may be enveloped by a pouch or the like to carry the coolant in an inconspicuous fashion.

It is reiterated that, in addition to a material coolant, such as ice or gel, an alternative embodiment of the present invention could comprise a Peltier device placed in direct contact with the condenser plate, thereby providing cooling means without the need to replenish melted coolant. Further, the system may be reversed, with reformulated refrigerant, such that the evaporator plate is outside the shoe, and the condenser plate is inside the shoe, to provide heat therapy to the foot. Also, the evaporator plate 18 of the present invention may be coated with thermal conducting mesh of metal or the like, or may be fabricated of a soft, flexible, thermal conductive material such as thermal putty, copper mesh or the like, to provide a conforming, relatively soft skin contact.

Figures 6, 7:
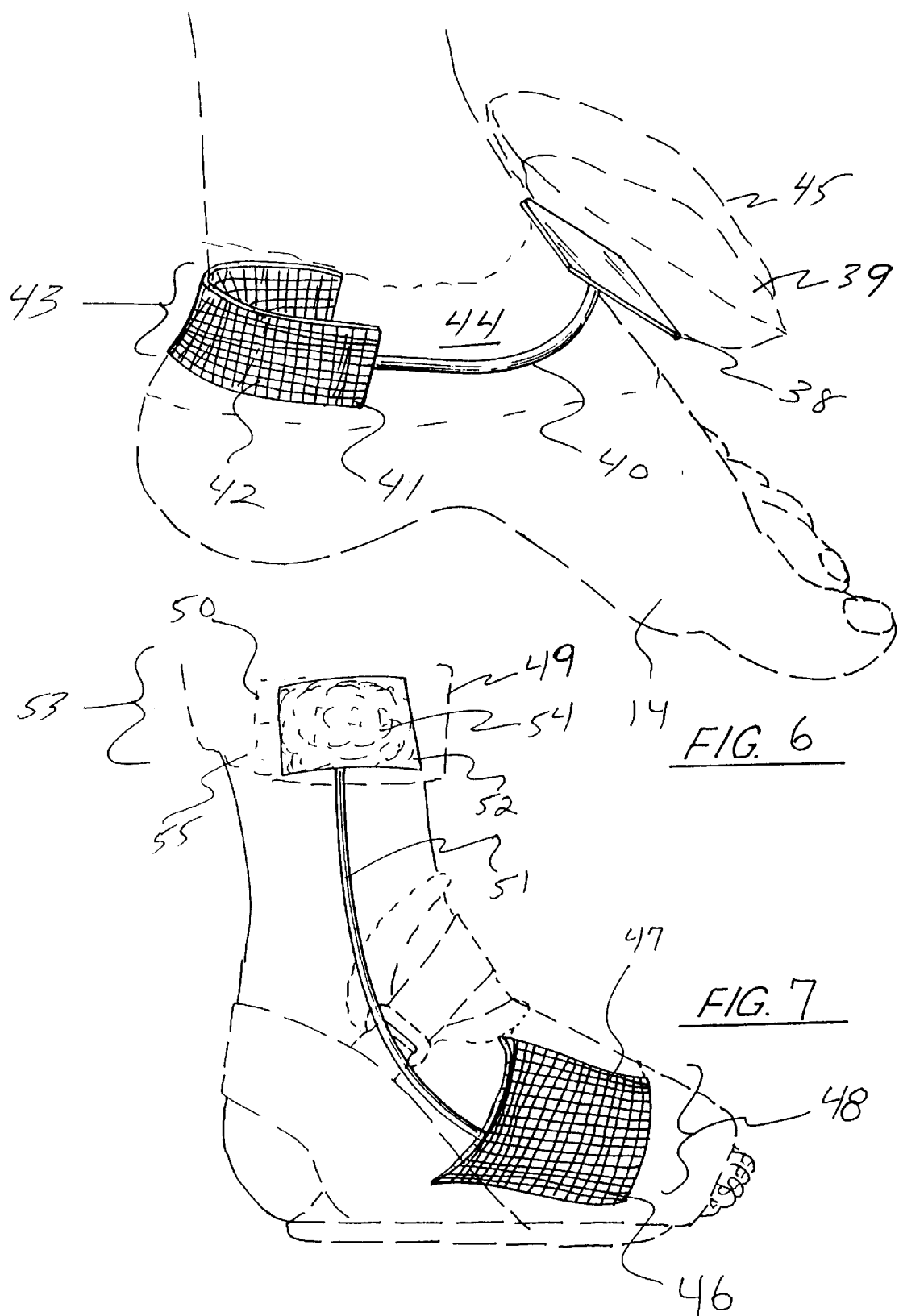
FIG. 6 illustrates a second alternative embodiment of the present invention, configured to treat Achilles heel, illustrating the device installed about a foot in phantom.
FIG. 7 illustrates a third alternative embodiment of the present invention, configured to treat an upper foot injury, illustrating the device installed about a foot in phantom.

A second alternative embodiment of the present invention is shown in FIG. 6, wherein there is provided a method of treating tendinitis of the Achilles tendon. As shown, an evaporator 41, which ideally is somewhat flexible for comfort, and thereby formed of some flexible thermally conductive material such as copper mesh 42 or thermal putty, is configured to contact and envelope the afflicted Achilles tendon area 43. A heat pipe 40 communicating with the evaporator 41 runs to a condenser plate 38 which may be situated along or above the upper foot 14 as shown and retained via support strap 44 of soft and insulating neoprene or the like, or may be strapped to the lower calf area of the leg.

The operation of the unit is the same as the other embodiment supra, that is, ice 39 (which may be enveloped by pouch 45 or insulating sleeve) initiates operation of the heat pipe, which allows evaporator 41 to cool the afflicted Achilles tendon area. The present item may be configured to be worn with footwear, or may be integrated into custom footwear, as desired. It is anticipated that an estimated twenty-thirty minute therapy of cold temperature (60–65 degrees F) should be provided with an ice pack of about 1.5 ounces with the present embodiment.

A third alternative embodiment of the present invention is shown in FIG. 7, wherein there is provided a method of treating an injury of the foot. As shown, an evaporator 46, which is again ideally somewhat flexible for comfort, and thereby formed of some flexible thermally conductive material such as copper or other conductive mesh 47 or thermal putty, is configured to contact and envelope the afflicted area 48. A heat pipe 51 communicating with the evaporator 46 runs to a condenser plate 52 which may be supported by, for example, the lower calf 53 as shown, and retained via support strap 49 of soft and insulating neoprene 55 or the like (although other materials are similarly suitable, including elastic cotton, polypropelene, and other materials), or may be strapped to another area of the foot or leg.

The operation of the unit is the same as the other embodiments supra, that is, ice 54 (which may be enveloped by pouch 50 or insulating sleeve) initiates operation of the heat pipe, which allows evaporator 46 to cool the afflicted area. The present item (and all of the embodiments) may be configured to be worn with a cast, splint, or may be integrated into custom footwear, as desired. Depending upon the surface area treated and the commensurate size of the evaporator and condensers, it is anticipated that an estimated twenty-thirty minute therapy of cold temperature (60–65 degrees F) should be provided with an ice pack of about 1.5 ounces with the present embodiment.

Figure 8:
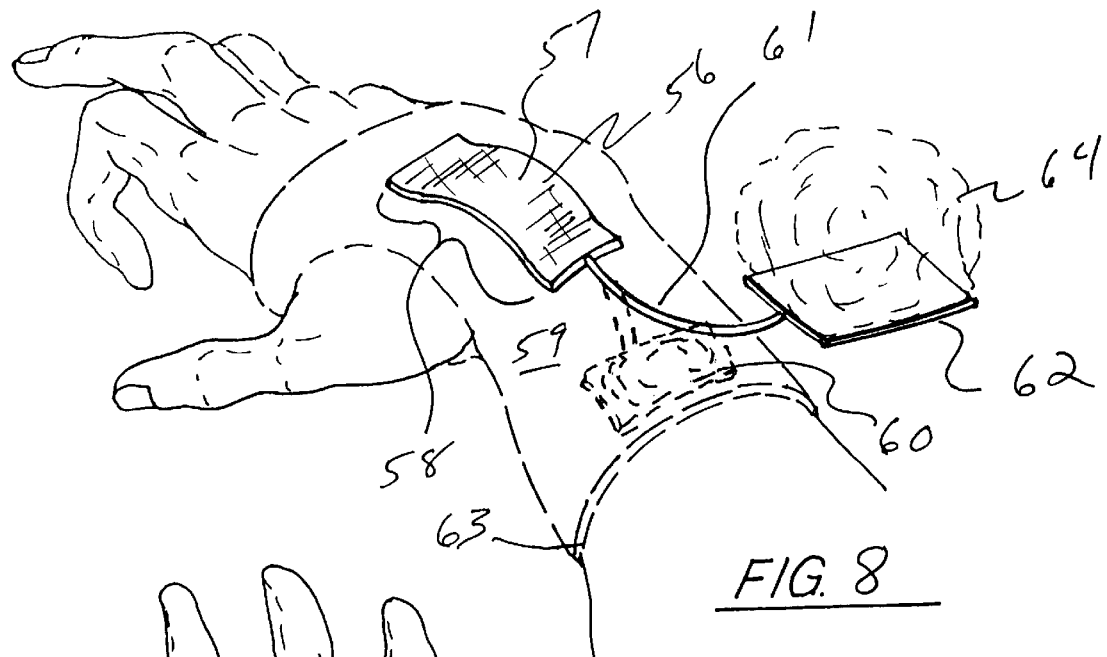
FIG. 8 illustrates a fourth alternative embodiment of the present invention, configured to treat a wrist injury, illustrating the device installed about a hand and wrist in phantom.
Figure 9:
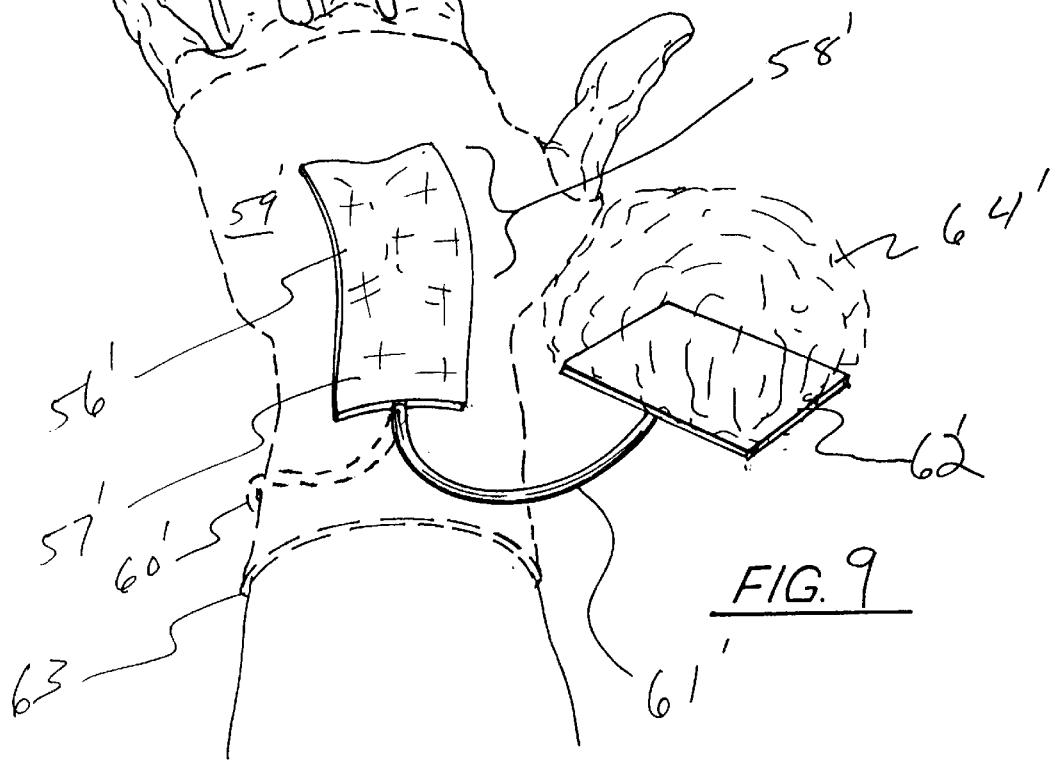
FIG. 9 illustrates a fourth alternative embodiment of the present invention, configured to treat an hand injury, illustrating the device installed about the hand in phantom.

A fourth and fifth alternative embodiment of the present invention is shown in FIGS. 8 and 9, respectively, wherein there is provided a method of treating alternative injuries to the wrist and hand. As shown, an evaporator 56, 56', which is again ideally somewhat flexible for comfort, and thereby formed of some flexible thermally conductive material such as conductive mesh 57, 57' or thermal putty, is configured to contact and envelope the afflicted area 58, 58'. A heat pipe 61, 61' communicating with the evaporator 56, 56' runs to a condenser plate 62, 62' which may be supported exteriorly, as shown, or supported (in phantom 60, 60') by the lower arm 63 and retained via support strap 59, 59' of soft and insulating neoprene or the like.

The operation of the unit is the same as the other embodiments supra, that is, ice 64, 64' (which may be enveloped by pouch in strap 59, 59') initiates operation of the heat pipe, which allows evaporator 56, 56' to cool the afflicted area. The present item (and all of the embodiments) may be configured to be worn with a cast, splint, garment, or the like, as desired.

Again, depending upon the surface area treated and the commensurate size of the evaporator and condensers, it is anticipated that an estimated twenty-thirty minute therapy of cold temperature (60–65 degrees F) should be provided with an ice pack of about 1.5 ounces with the present embodiment.

Figure 10:
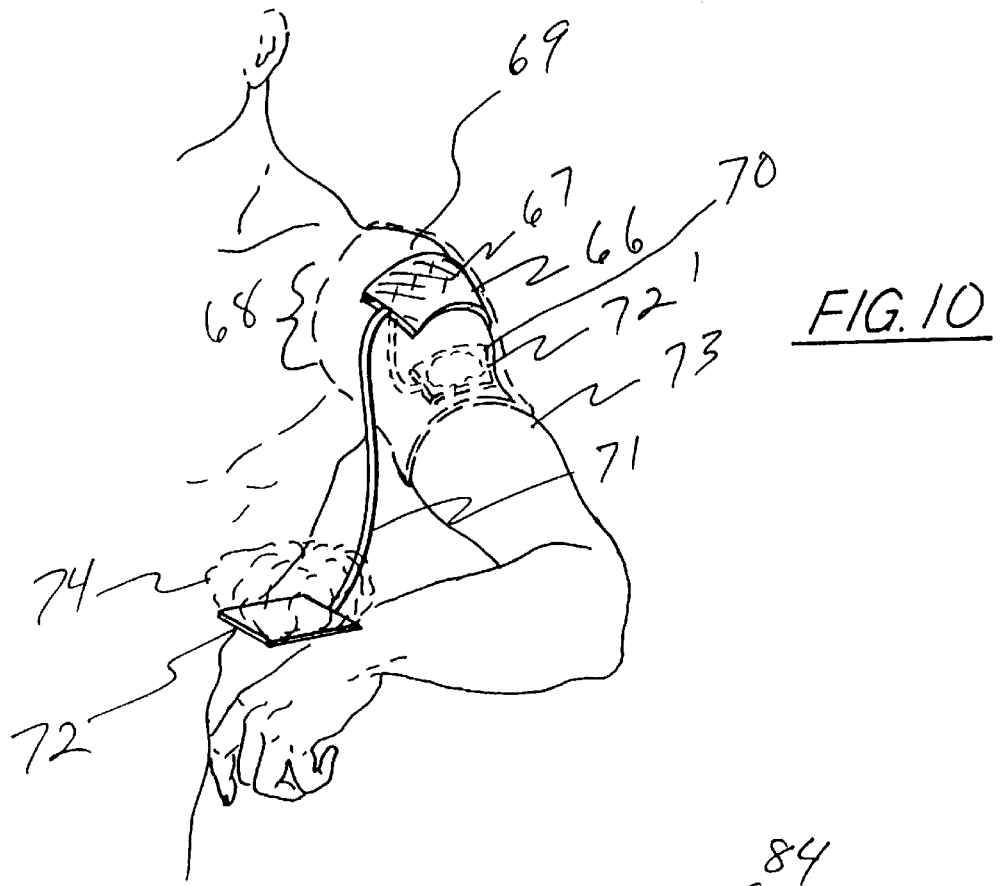
FIG. 10 illustrates a fifth alternative embodiment of the present invention, configured to treat a shoulder injury, illustrating the device installed about a patient in phantom.

A sixth alternative embodiment of the present invention is shown in FIG. 10, wherein there is provided a method of treating an injury of the shoulder. As shown, an evaporator 66, which is again ideally somewhat flexible for comfort, and thereby formed of some flexible thermally conductive material such as conductive mesh 67 or thermal putty (although a sold, formed evaporator plate anatomically shaped could be adequate), is configured to contact and envelope the afflicted area 68. A heat pipe 71 communicating with the evaporator 66 runs to a condenser plate 72 which may be supported exteriorly, as shown, or by, for example, the upper arm 73 as shown in phantom 72', and retained via support strap 69 of, for example, soft, insulating neoprene or the like (although other materials are similarly suitable, including elastic cotton, polypropelene, and other materials), or may be strapped to another area of the foot or leg.

The operation of the unit is the same as the other embodiments supra, that is, ice 74 (which may be enveloped by pouch 70 or insulating sleeve) initiates operation of the heat pipe, which allows evaporator 66 to cool the afflicted area. The present item (and all of the embodiments) may be configured to be worn with a cast, splint, or garment or device, as desired. Depending upon the surface area treated and the commensurate size of the evaporator and condensers, it is anticipated that an estimated twenty-thirty minute therapy of cold temperature (60–65 degrees F) could be provided with an ice pack of about 2–3 ounces with the present embodiment.

Figure 11:
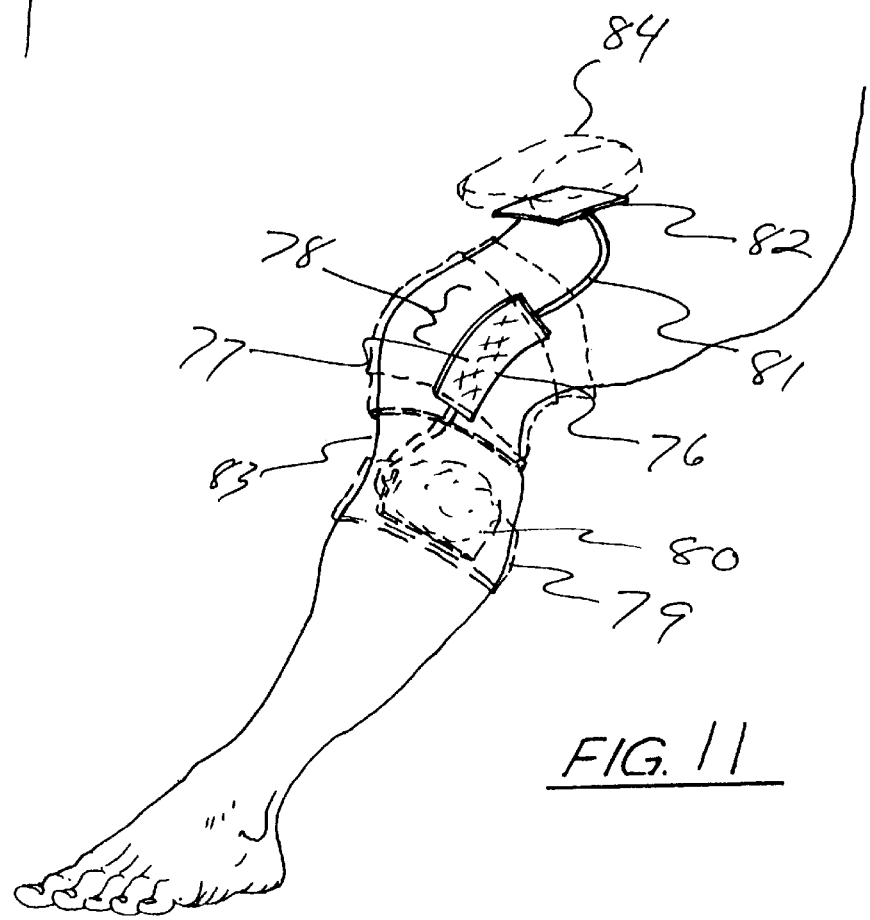
FIG. 11 illustrates a sixth alternative embodiment of the present invention, configured to treat a knee injury, illustrating the device installed about a leg in phantom.

A seventh alternative embodiment of the present invention is shown in FIG. 11, wherein there is provided a method of treating an injury of the knee. As shown, an evaporator 76, which is again ideally somewhat flexible for comfort, and thereby formed of some flexible thermally conductive material such as conductive mesh 77 or thermal putty, is configured to contact and envelope the afflicted area 78. A heat pipe 81 communicating with the evaporator 76 runs to a condenser plate 82 which may be supported by, for example, the upper calf 83 as shown, and retained exteriorly above the thigh, as shown, or via support strap 79 (in phantom).

The operation of the unit is the same as the other embodiments supra, that is, ice 84 (which may be enveloped by pouch 80 or insulating sleeve) placed upon condenser 80 initiates operation of the heat pipe, which allows evaporator 76 to cool the afflicted area. The present item (and all of the embodiments) may be configured to be worn with a cast, splint, or other medical device or garment, as desired. Depending upon the surface area treated and the commensurate size of the evaporator and condensers, it is anticipated that an estimated twenty-thirty minute therapy of cold temperature (60–65 degrees F) should be provided with an ice pack of about 1.5 ounces with the present embodiment.

Figure 12:
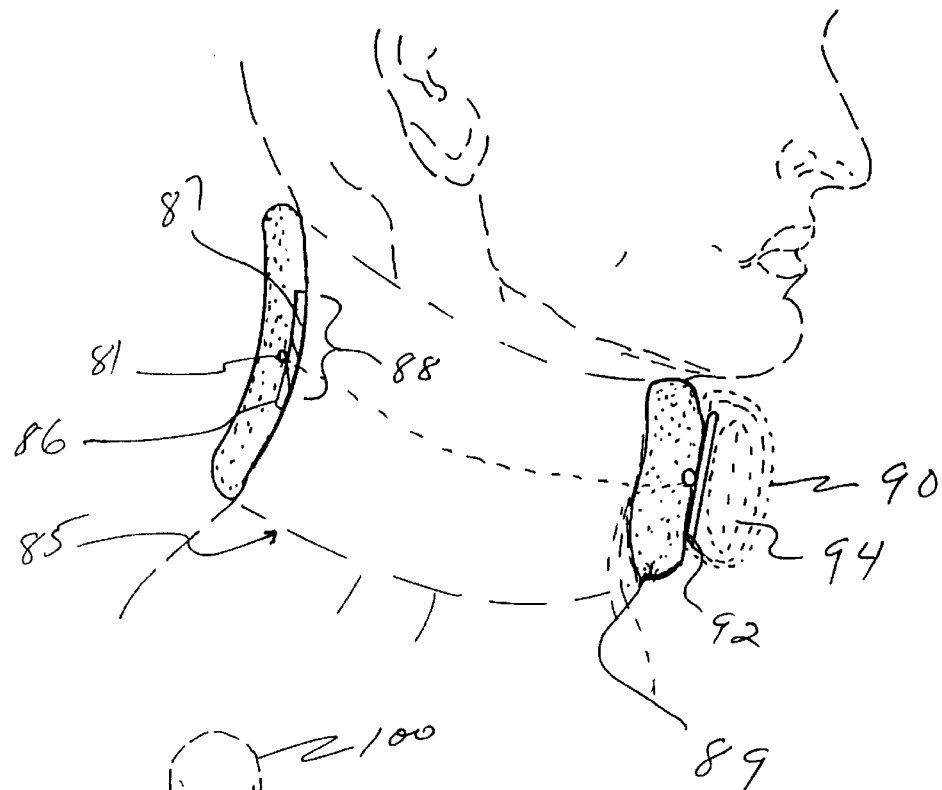
FIG. 12 illustrates a seventh alternative embodiment of the present invention, configured to treat a neck injury, illustrating the device installed about a patient in phantom.

A eighth alternative embodiment of the present invention is shown in FIG. 12, wherein there is provided a method of treating an injury of the spine/neck 85. As shown, an evaporator 86, which is again ideally somewhat flexible for comfort, and thereby formed of some flexible, thermally conductive material, such as conductive mesh 87 or thermal putty, is configured to contact and envelope the afflicted area 88. It is, however, noted that a solid, non-flexible evaporator plate, shaped to configure the anatomical region to which it contacts, may be likewise acceptable, especially since a solid evaporator plate would be expected to provide superior thermal transfer over flexible transfer materials.

A heat pipe 81 communicating with the evaporator 86 runs to a condenser plate 92 which may be supported by, for example, the neck 85 as shown, and retained via support strap 89 similar to neck collars currently in use.

The operation of the unit is the same as the other embodiments supra, that is, ice 94 (which may be enveloped by pouch 90 or insulating sleeve) placed into contact with the condenser plate initiates operation of the heat pipe, which allows evaporator 86 to cool the afflicted area. The present embodiment could also be implemented with a cast or traction equipment or garment or other medical equipment or devices, as desired. Depending upon the surface area treated and the commensurate size of the evaporator and condensers, it is anticipated that an estimated twenty-thirty minute therapy of cold temperature (60–65 degrees F) could be provided with an ice pack of about 1.5 ounces with the present embodiment.

Figure 13:
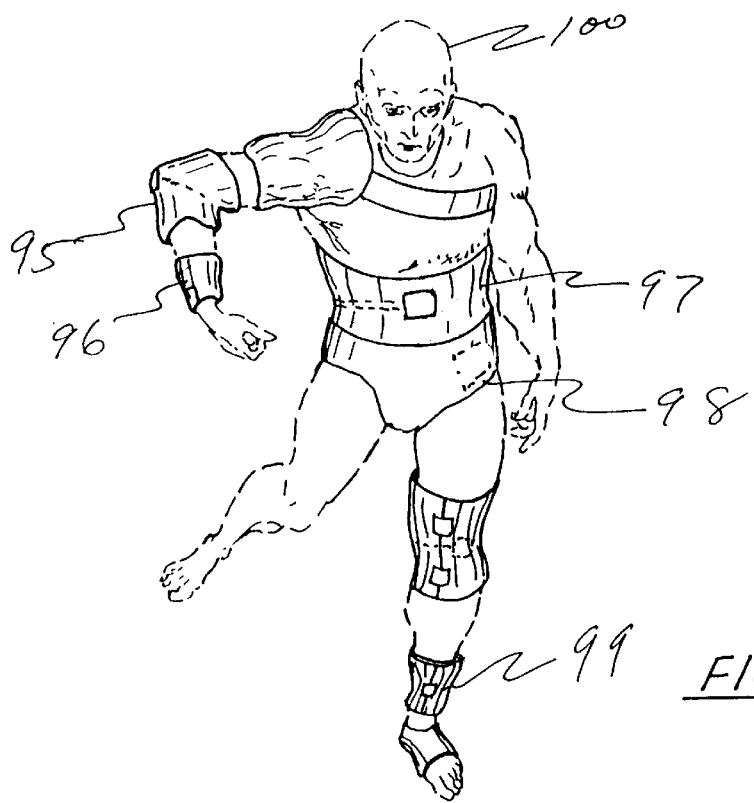
FIG. 13 illustrates various embodiments of the present invention installed about a patient.

FIG. 13 illustrates various other areas of treatment utilizing the method of cooling an afflicted area of the present invention, that is, providing a support for affixing the evaporator plate in the vicinity of the afflicted area, providing a condenser and coolant such as ice for cooling the condenser, and providing a heat pipe running form the evaporator plate to the condenser plate to facilitate cooling of the evaporator plate. Besides the above areas, the present invention can be utilized in many other areas, including the head 100, elbow 95, forearm 96, back 97, hip 98, and shin 99.

FIGS. 14A–14C illustrate the ninth embodiment of the present invention, wherein there is shown a method and apparatus for treating an injury to the lower back. As shown, a back belt 109 having first 110 and second 111 ends with a medial area 112 therebetween, and an inside 113 and an outside 114 is provided. An evaporator 106, which is again ideally somewhat flexible for comfort, and thereby formed of some flexible thermally conductive material such as conductive mesh or thermal putty or the like, is situated in the inside 113 medial area 112 of the belt 109, and is configured to contact and envelope the afflicted area 108 of the patient 105. A heat pipe 101 communicating with the evaporator 106 runs to a condenser plate 102 which may be supported by, for example, the outside of the belt, the belt affixed to the patient 105 via contact fasteners 103, 103'.

The operation of the unit is the same as the other embodiments supra, that is, ice 103 (which may be enveloped by pouch 104 or insulating sleeve) initiates operation of the heat pipe 101, which allows evaporator 106 to cool the afflicted area 108. The present item (and all of the embodiments) may also be configured to be worn with a cast, splint, garment, or traction equipment, as desired. Depending upon the surface area treated and the commensurate size of the evaporator and condensers, it is anticipated that an estimated twenty-thirty minute therapy of cold temperature (60–65 degrees F) could be provided with an ice pack of about three to four ounces with the present embodiment.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. An apparatus for providing thermal application to an external body area of a patient, comprising:

a heat pipe having first and second ends and a length, first and second thermally conductive members, said first thermally conductive member communicating with said first end of said heat pipe, said second thermally conductive member communicating with said second end of said heat pipe;

said first thermally conductive member formed to communicate with said external body area of said patient, retaining means for retaining said first thermally conductive member to said external body area of said patient; and thermal means for thermally affecting said second thermally conductive member; in such a manner as to facilitate a change in temperature in said first thermally conductive member by utilizing said heat pipe as a thermal transfer conduit between said first and second thermally conductive members.

2. The apparatus of claim 1, wherein said thermal means comprises ice.

3. The apparatus of claim 1, wherein said retaining means comprises an insole configured to communicate with the bottom of a foot, and wherein said first thermally conductive member is configured to communicate with said bottom of said foot.

4. The apparatus of claim 1, wherein said first thermally conductive member comprises an evaporator, and wherein said second thermally conductive member comprises a condenser.

5. The apparatus of claim 4, wherein said retaining means comprises an insole configured to communicate with the bottom of a foot, and wherein said first thermally conductive member is configured to communicate with said bottom of said foot, and wherein said thermal means comprises ice placed in communication with said condenser.

6. The apparatus of claim 5, wherein said insole further includes a vertical support member having first and second ends, said first end communicating with said insole, said second end communicating with said condenser, said vertical support member at least partially enveloping said heat pipe.

7. The apparatus of claim 6, wherein said insole is configured to fit within an article of footwear such that said vertical support member supports said condenser outside of said article of footwear.

8. The apparatus of claim 5, wherein said insole forms an article of footwear.

9. The apparatus of claim 4, wherein said retaining means comprises a back belt having first and second ends with a medial area therebetween, an inside, and an outside, said back belt further having situated along said inside of said back belt, along said medial area of said back belt, said first thermally conductive member.

10. The apparatus of claim 4, wherein said retaining means comprises a knee brace.

11. The apparatus of claim 4, wherein said first thermally conductive member is shaped to communicate with said external body area of said patient.

12. The apparatus of claim 11, wherein said first thermally conductive member is formed to envelope a portion of the lower Achilles tendon.

13. The apparatus of claim 11, wherein said first thermally conductive member is formed to envelope a portion of the upper foot.

14. The apparatus of claim 4, wherein said first thermally conductive member is formed of flexible thermally conductive material.

15. The apparatus of claim 14, wherein said flexible thermally conductive material is thermal putty.

16. The apparatus of claim 14, wherein said flexible thermally conductive material is a thermally conductive mesh.

17. The apparatus of claim 4, wherein said retaining means comprises a neck brace having first and second ends with a medial area therebetween, an inside, and an outside, said neck brace further having situated along said inside of said neck brace, along said medial area of said neck brace, said first thermally conductive member.

18. The apparatus of claim 17, wherein said neck brace envelopes said heat pipe, and wherein said second thermally conductive member is situated along said outside of said neck brace, and wherein there is further provided thermal retaining means to retain said thermal means to said second thermally conductive member.

19. The apparatus of claim 18, wherein said thermal means comprises ice.

20. The apparatus of claim 4, wherein said retaining means comprises a cast.

21. The apparatus of claim 4, wherein said retaining means comprises a brace.

22. The apparatus of claim 4, wherein said retaining means comprises a bandage.

23. The apparatus of claim 1, wherein said thermal means comprises a Peltier. effect device.

24. The method of providing localized thermal application to an afflicted external body area of a patient, comprising the steps of:
   a. providing a heat pipe having first and second ends and a length,
      a first thermally conductive member communicating with said first end of said heat pipe, said first thermally conductive member configured to communicate with said external body area of said patient,
      a second thermally conductive member communicating with said second end of said heat pipe;
   b. placing said first thermally conductive member in communication with an afflicted external body area;
   c. applying thermal means to said second thermally conductive member, so as to thermally affect said second thermally conductive member,
   d. said second thermally conductive member conducting said thermal affect to said heat pipe, providing a thermally affected heat pipe;
   e. said thermally affected heat pipe conducting said thermal affect to said first thermally conductive member, so as to thermally affect said afflicted external body area in communication with said first thermally conductive member.

25. The method of providing localized thermal application to an afflicted external body area of a patient, comprising the steps of:
   a. providing a heat pipe having first and second ends and a length,
      an evaporator communicating with said first end of said heat pipe, said evaporator configured to communicate with said external body area of said patient,
      a condenser communicating with said second end of said heat pipe;
   b. placing said evaporator in communication with an afflicted external body area;
   c. applying chilling means to chill said condenser, allowing said heat pipe to cool said evaporator;
   d. cooling said afflicted external body area in communication with said evaporator.

26. The method of treating plantar fasciitis, comprising the steps of:
   a. providing a heat pipe having first and second ends and a length, an evaporator communicating with said first end of said heat pipe, said evaporator configured to communicate with said external body area of said patient, a condenser communicating with said second end of said heat pipe;

b. placing said evaporator in communication with said afflicted area;

c. applying chilling means to chill said condenser, allowing said heat pipe to cool said evaporator;

d. cooling said afflicted area in communication with said evaporator.

27. An apparatus for treating plantar fasciitis, comprising:

a heat pipe having first and second ends, and a length;

an evaporator communicating with said first end of said heat pipe, said evaporator configured to communicate with said external body area of said patient, a condenser communicating with said second end of said heat pipe an insole having a top area configured to engage a foot, said insole having situated thereupon said evaporator, said insole further comprising a vertical support member formed of insulative material having first and second ends, said iertical support member configured to at least partially envelope said heat pipe, said first end of said vertical support member emanating from said insole, said second end of said vertical support member situated in the vicinity of said condenser;

chilling means for chilling said condenser and thereby chill said second end of said heat pipe, thermally affecting said heat pipe so as to facilitate evaporative cooling of said evaporator.

28. The apparatus of claim 27, wherein said thermal means comprises ice.

29. The apparatus of claim 27, wherein said thermal means comprises a Peltier effect device.

30. An apparatus for providing thermal application to an external body area of a patient, comprising:

a heat pipe having first and second ends and a length, first and second thermally conductive members, said first thermally conductive member communicating with said first end of said heat pipe, said second thermally conductive member communicating with said second end of said heat pipe;

said first thermally conductive member configured to communicate with said external body area of said patient, retaining means for retaining said first thermally conductive member to said external body area of said patient; and thermal means for thermally affecting said second thermally conductive member, said heat pipe insulated along its length to prevent direct heat transfer between said length of said heat pipe and said external body area.

* * * * *

UNITED STATES PATENT AND TRADEMARK OFFICE
CERTIFICATE OF CORRECTION

PATENT NO : 6,074,414
DATED : June 13, 2000
INVENTOR(S) : Michael Haas, Richard Bailey, Lee Barberito, Jerome F. Krentel et al It is certified that error appears in the above-identified patent and that said Letters Patent are hereby corrected as shown below: On the title page:

Cover Sheet, please change the assignee to read -- Cimex Bio-Tech L.C., Covington, La. --.

Cover Sheet, please change the Attorney, Agent or Firm to read -- Joseph T. Regard, Ltd. --.

Signed and Sealed this

Twenty-fourth Day of April, 2001

Attest:

NICHOLAS P. GODICI

Attesting Officer

Acting Director of the United States Patent and Trademark Office